United States Patent [19]

Rogers et al.

[11] Patent Number: 5,607,468
[45] Date of Patent: Mar. 4, 1997

[54] METHOD OF MANUFACTURING AN INTRALUMINAL STENTING GRAFT

[75] Inventors: Russell L. Rogers, Munith; Rodney E. Turk, W. Bloomfield, both of Mich.

[73] Assignee: Aeroquip Corporation, Maumee, Ohio

[21] Appl. No.: 516,883

[22] Filed: Aug. 18, 1995

Related U.S. Application Data

[62] Division of Ser. No. 334,524, Nov. 4, 1994, Pat. No. 5,534,024.

[51] Int. Cl.$^6$ ............................ A61F 2/06; A61F 2/04
[52] U.S. Cl. ............................ 623/1; 623/12; 600/36
[58] Field of Search ............................ 623/1, 11, 12; 606/191, 194, 195, 198, 151, 153; 600/36; 604/8

[56] References Cited

U.S. PATENT DOCUMENTS

| | | | |
|---|---|---|---|
| 4,195,623 | 4/1980 | Zeff et al. | 128/1 |
| 4,195,637 | 4/1980 | Gruntzig et al. | 128/348 |
| 4,271,839 | 6/1981 | Fogarty et al. | 128/344 |
| 4,386,601 | 6/1983 | Trick | 128/1 |
| 4,508,112 | 4/1985 | Seeler | 128/89 |
| 4,577,631 | 3/1986 | Kreamer | 128/334 |
| 4,649,914 | 3/1987 | Kowalewski | 128/207 |
| 4,733,665 | 3/1988 | Palmaz | 128/343 |
| 4,739,762 | 4/1988 | Palmaz | 128/343 |
| 4,740,207 | 4/1988 | Kreamer | 623/1 |
| 4,762,130 | 8/1988 | Fogarty et al. | 128/348 |
| 4,769,029 | 9/1988 | Patel | 623/1 |
| 4,774,949 | 10/1988 | Fogarty | 128/348 |
| 4,776,337 | 10/1988 | Palmaz | 128/1 |
| 4,787,899 | 11/1988 | Lazarus | 623/1 |
| 4,793,348 | 12/1988 | Palmaz | 128/325 |
| 4,795,458 | 1/1989 | Regan | 623/1 |
| 4,877,025 | 10/1989 | Hanson | 128/207 |
| 4,955,895 | 9/1990 | Sugiyama et al. | 606/194 |
| 5,156,620 | 10/1992 | Pigott | 623/1 |

*Primary Examiner*—Debra S. Brittingham
*Attorney, Agent, or Firm*—Emch, Schaffer, Schaub & Porcello Co., L.P.A.

[57] ABSTRACT

An intraluminal stenting graft for implantation in a blood vessel and a method for making same wherein the intraluminal stenting graft includes a collapsible tube member having a first end and a second end. An outer layer and an inner layer extend between the ends. The outer layer is more flexible than the inner layer. The outer layer is joined to the inner layer to form a plurality of cylinders longitudinally extending between the first end and the second end. The method of the present invention including the steps of: placing a first layer of material on a substantially flat surface; placing a second layer of material on a shaped surface; maintaining the second layer on said shaped surface by use of reverse pressure; moving the second layer to the first layer; joining the second layer to the first layer to form a plurality of longitudinally extending cylinders; and shaping the first and second layers to form a tube member.

7 Claims, 4 Drawing Sheets

METHOD OF MANUFACTURING AN INTRALUMINAL STENTING GRAFT

This is a divisional of application(s) Ser. No. 008/334,524 filed on Nov. 4, 1994 now U.S. Pat. No. 5,534,024.

DESCRIPTION

1. Background Art

The present invention is directed to an intraluminal stenting graft. More specifically, the invention is directed to an intraluminal stenting graft for implantation in a blood vessel including a collapsible tube member formed from a plurality of cylinders. The invention is further directed to a method for making such a stenting graft.

Intraluminal stenting grafts are known in the art. An example of an intraluminal stenting graft/stent is disclosed in U.S. Pat. No. 5,156,620, which is incorporated herein by reference. Intraluminal stenting grafts are implanted in a blood vessel to repair, for example, aortic aneurysms. They are also used to support sections of a blood vessel that are diseased or have become narrowed by arteriosclerosis.

2. Disclosure of Invention

The present invention is directed to an intraluminal stenting graft for implantation in a blood vessel and a method for making same. The intraluminal stenting graft includes a collapsible tube member having a first end and a second end. An outer layer and an inner layer extend between the ends. The outer layer is more flexible than the inner layer. The outer layer is joined to the inner layer to form a plurality of cylinders longitudinally extending between the first end and the second end.

The method of the present invention includes the steps of:

(a) placing a first layer of material on a substantially flat surface;

(b) placing a second layer of material on a shaped surface;

(c) maintaining the second layer on said shaped surface by use of reverse pressure;

(d) moving the second layer to the first layer;

(e) joining the second layer to the first layer to form a plurality of longitudinally extending cylinders; and (f) shaping the first and second layers to form a tube member.

The primary object of the present invention is to provide an intraluminal stenting graft that is efficient.

An important object of the present invention is to provide an intraluminal stenting graft that is relatively easy to use.

Other objects and advantages of the invention will become apparent upon a review of the accompanying drawings and the following detailed description of the invention.

BRIEF DESCRIPTION OF THE DRAWINGS

FIG; 10 is a view similar to the view of FIG. 9 showing the joining of the second layer to the first layer.

BEST MODE FOR CARRYING OUT INVENTION

Figure 1:
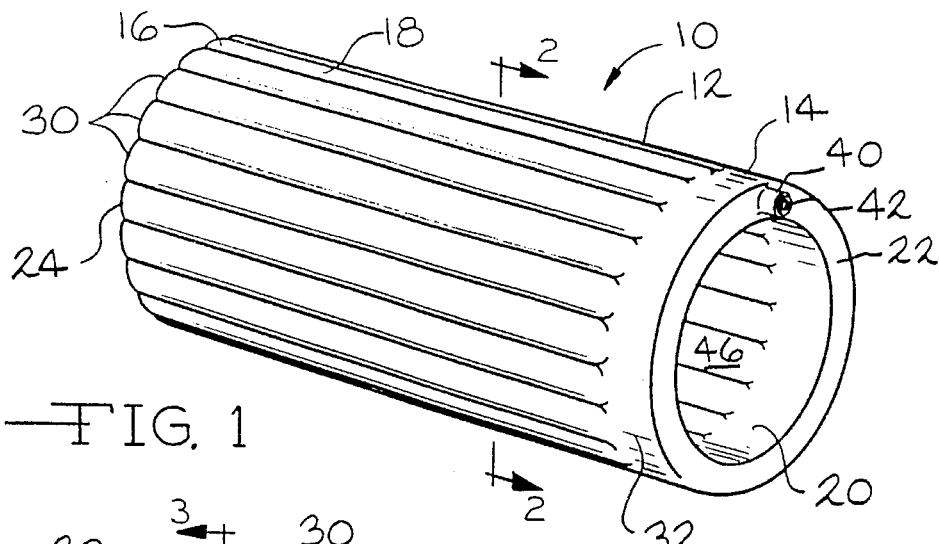
FIG. 1 is a perspective view of a first embodiment of an intraluminal stenting graft according to the present invention.
Figure 2:
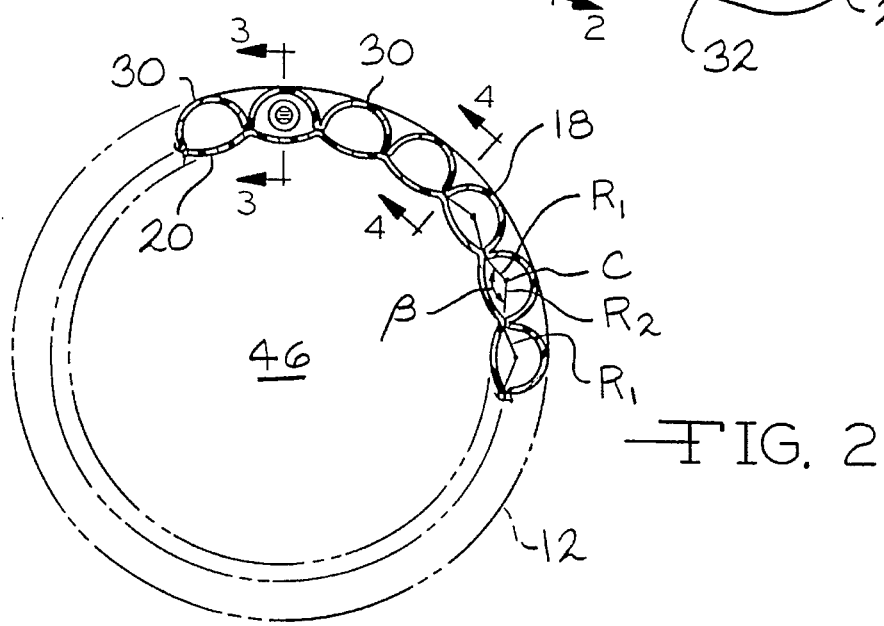
FIG. 2 is a cross-sectional view of the plurality of cylinders of the present invention taken along line 2—2 of FIG. 1.

Referring now to the drawings, the present invention will now be described in detail. Referring to FIGS. 1 and 2, the intraluminal stenting graft of the present invention is indicated by the reference number 10. The stenting graft 10 includes a collapsible tube member 12 having a first end 14 and a second end 16. An outer layer of material 18 and an inner layer of material 20 extend between said first end 14 and said second end 16. A first end wall 22 extends between the outer layer 18 and the inter layer 20 at the first end 14. A second end wall 24 extends between the outer layer 18 and the inner layer 20 at the second end 16.

Figure 4:
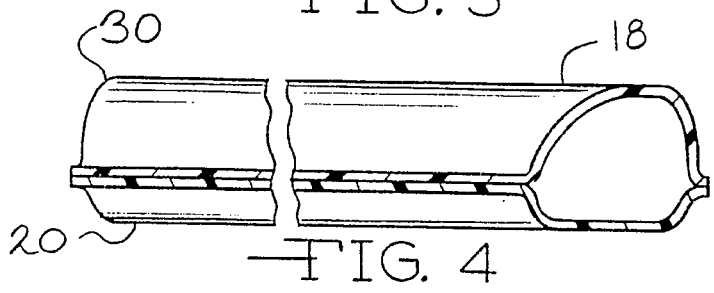
FIG. 4 is a cross-sectional view taken along line 4—4 of FIG. 2 showing one of the cylinders according to the present invention.

As shown in FIGS. 1, 2 and 4, the outer layer 18 is joined to the inner layer 20 to form a plurality of cylinders 30 that extend longitudinally between the first end 14 and the second end 16. As shown in FIG. 1, the tube member 12 can include a radially extending chamber 32 that is in communication with the plurality of cylinders 30. In the present embodiment, the chamber 32 is positioned adjacent the first end 14. However, it should be understood that the chamber 32 can be positioned in a variety of locations along the length of the chamber.

Figure 3:
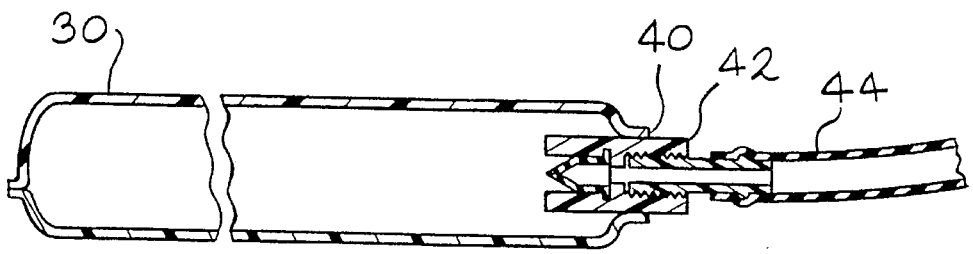
FIG. 3 is a cross-sectional view taken along line 3—3 of FIG. 2 showing the one-way valve of the present invention positioned in the opening in the end wall of the tube member.

Referring to FIG. 1, the tube member 12 can include an opening 40 in the first end wall 22, The opening 40 can receive a fluid, such as air. As described below, the fluid causes the collapsed tube member 12 to expand for implantation in a blood vessel. As shown in FIG. 3, a one-way valve 42, such as a check valve, can be positioned in the opening 40. The valve 42 allows for the introduction of the fluid into the tube member 12. The valve prevents the escape of the fluid from the tube member 12 after introduction into the tube member. The fluid can be introduced into the tube member 12 through the valve 42 by a fluid conduit 44.

Referring to FIG. 2, the outer layer 18 and the inner layer 20 are composed of a polymer material that is biocompatible. An example of such a material is polytetrafluoroethylene. The outer layer 18 is constructed of a more flexible or lighter weight material than the inner layer 20. This allows the outer layer 18 to be more compliant when the tube member 12 is expanded. The inner layer 20 can be treated or coated with a material such as expanded polytetrafluoroethylene (ePTFE) to create a surface more conducive to blood flow.

As shown in FIG. 2, each of the cylinders 30 includes a centerline C that extends longitudinally through the cylinder when the tube member 12 is in an expanded condition. The centerline C is a point from which two radii $R_1$ and $R_2$ extend. The radii $R_1$ and $R_2$ define an angle $\beta$. The angle $\beta$ can be an obtuse angle being more than 90° and less than 180°. When the plurality of cylinders 30 are positioned adjacent one another to form the tube member 12, as shown in FIG. 2, the radius $R_1$ of one of the cylinders bisects the radius $R_2$ Of the adjacent cylinder. This arrangement causes the plurality of cylinders 30 to cooperate to maintain the tube member 12 in a stable, expanded condition for implantation in a blood vessel. It has been found that the greater compliance of the outer layer 18 and the greater amount of material of the outer layer 18 as compared to the inner layer 20 causes the angle $\beta$ to be less than 180°. When the tube member 12 is expanded, the plurality of cylinders 30 interfere with one another to force the tube member into a round configuration as shown in FIG. 1. This provides an open pathway 46 for the flow of blood in a blood vessel.

Figure 5:
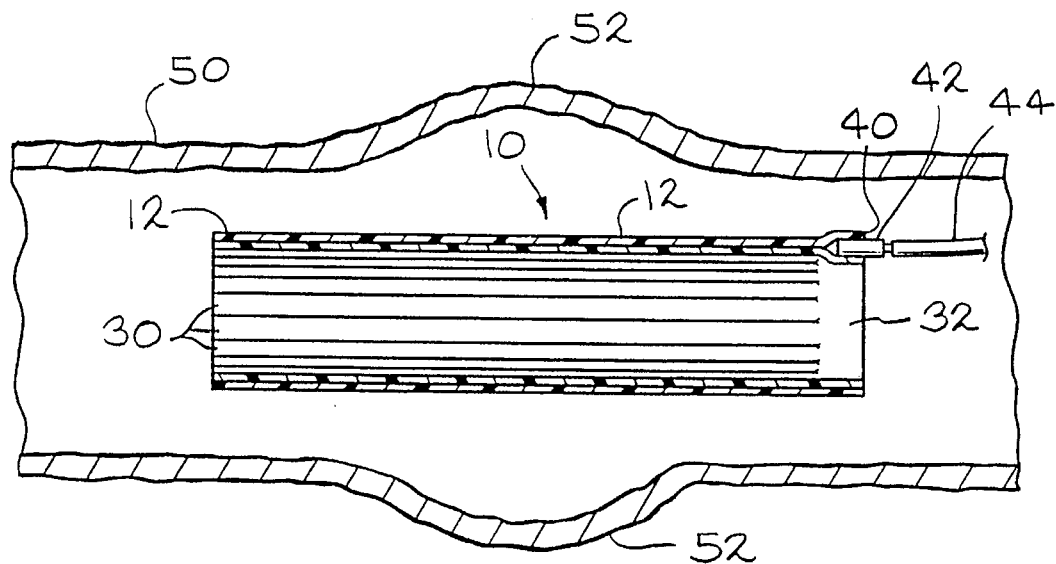
FIG. 5 is a cross-sectional view of the intraluminal stenting graft of the present invention positioned in a blood vessel at the site of implantation in a collapsed condition.
Figure 6:
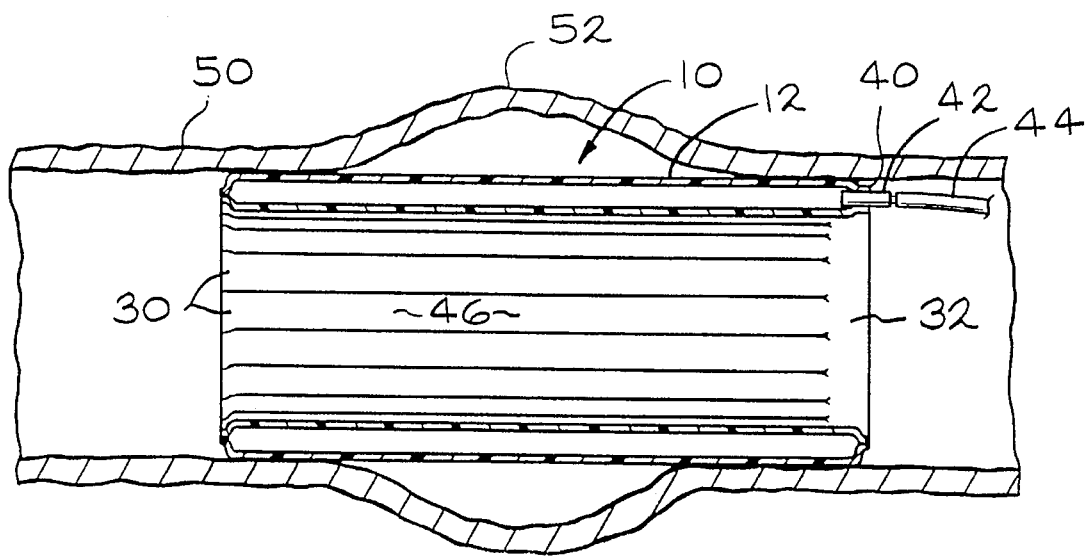
FIG. 6 is a cross-sectional view similar to the view of FIG. 5 showing the intraluminal stenting graft implanted in a blood vessel.

Referring now to FIGS. 5 and 6, the intraluminal stenting graft 10 of the present invention is implanted in a blood vessel 50 by manipulating the collapsed tube member 12 through the vessel to an implantation site 52. The tube member can be manipulated by the conduit 44, which is in communication with the valve 42, or by some other suitable apparatus. As shown in FIG. 6, when the stenting graft 10 is in the proper position, fluid from the conduit 44 is introduced through the opening 40 and into the chamber 32 and cylinders 30. The chamber 32 allows for an efficient distribution of fluid into the cylinders 30. As described above, the plurality of cylinders 30 and the outer and inner layers 18 and 20, respectively, cooperative to maintain the tube member 12 in a round and open configuration. After filling, the conduit 44 is removed. The stenting graft 10 allows blood flow through the pathway 46 at the site of implantation 52.

Figure 7:
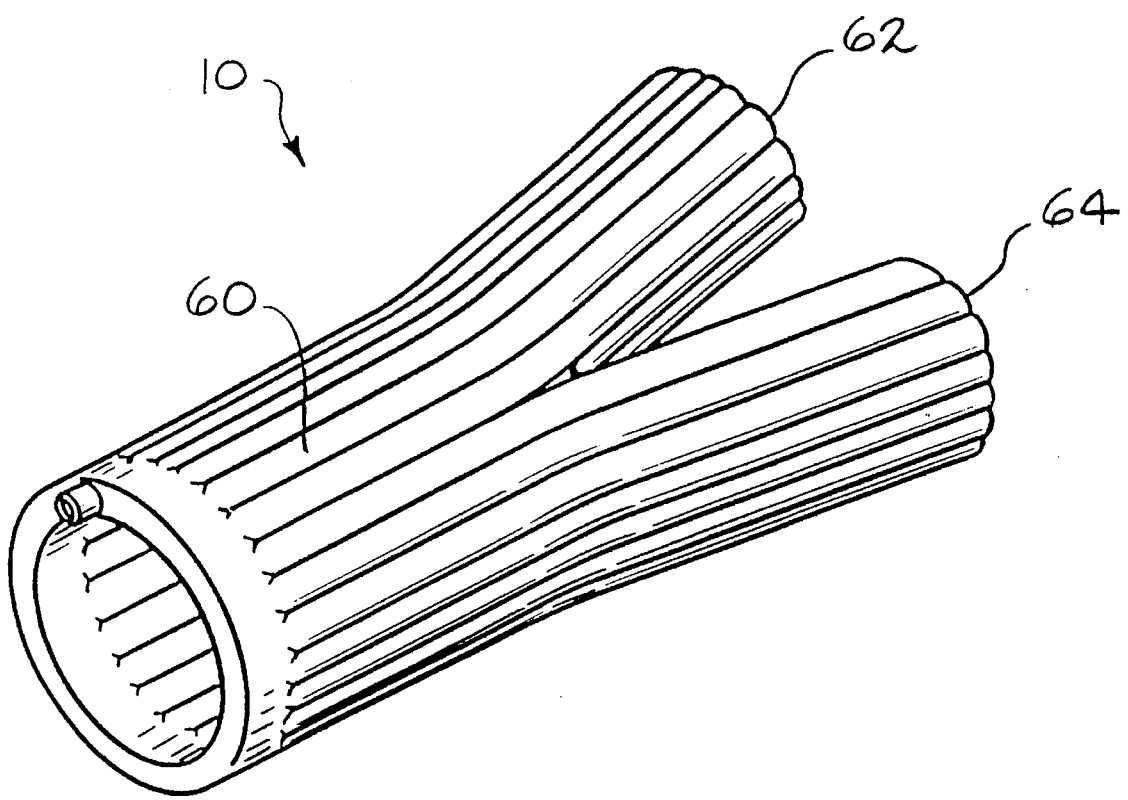
FIG. 7 is a second embodiment of an intraluminal stenting graft according to the present invention.

A second embodiment of the intraluminal stenting graft 10 of the present invention is shown in FIG. 7. The stenting graft 10 includes a trunk portion 60 and branch portions 62 and 64. This embodiment can be used, for example, at the bifurcation of the aorta and lilac arteries. The trunk portion 60 can be positioned in the aorta and the branch portions 62 and 64 can be positioned in the lilac arteries. Many other configurations can be constructed depending on the application.

Figure 8:
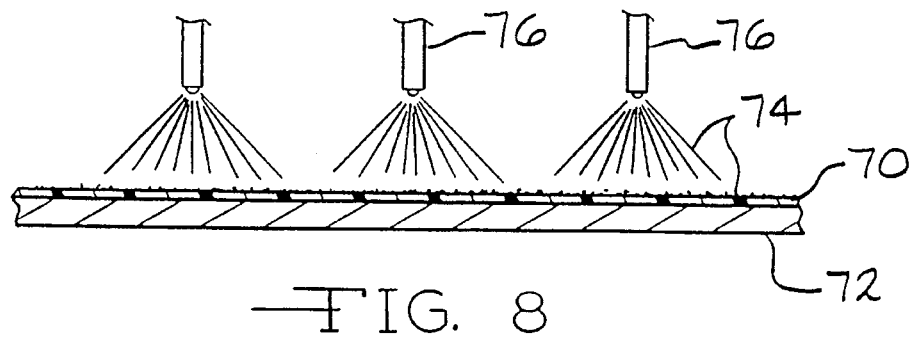
FIG. 8 is a side elevational view of the first layer of material on a platen being treated according to the method of the present invention.

Referring now to FIGS. 8 through 11, the method for manufacturing an intraluminal stenting graft according to the present invention will be described in detail. Referring to FIG. 8, a first layer of material 70, which corresponds to the inner layer 20, is placed on a flat surface such as a platen 72. A bonding agent such as adhesive 76 is applied to the first layer 70 by applicators 78.

Figure 9:
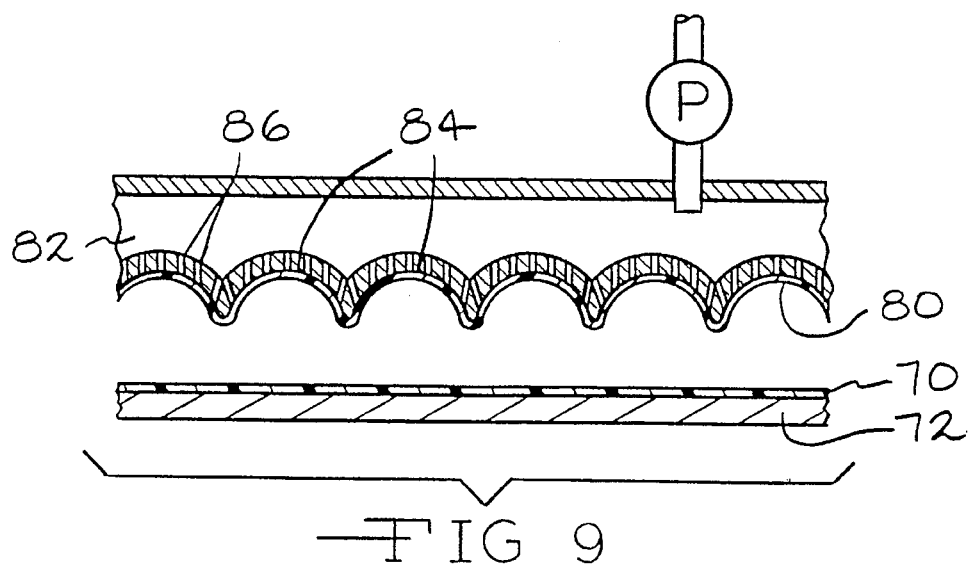
FIG. 9 is a side elevational view showing the second layer of material on a shaped surface being maintained on the surface by reverse pressure according to the method of the present invention.

As shown in FIG. 9, a second layer of material 80, which corresponds to the outer layer 18, is placed on a shaped surface 82. The shaped surface 82 includes longitudinally extending indentations 84 having, for example, partially cylindrical shapes. The indentations include a coating 86 of synthetic resin polymers and products, such as Teflon®, to prevent the second layer 80 from adhering to the shaped surface 82. The second layer 80 is maintained on the shaped surface 82 by the use of reverse pressure or vacuum created by a reversible pump P.

Figure 10:
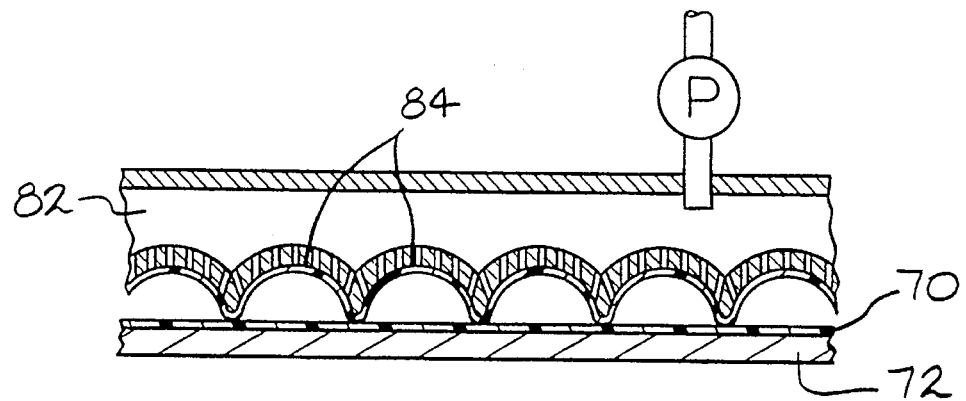

As shown in FIG. 10, the second layer 80 is moved to the first layer 70. The layers 70 and 80 are fixedly joined together by the adhesive 74. The layers can also be joined by a heat sealing process (not shown).

Figure 11:
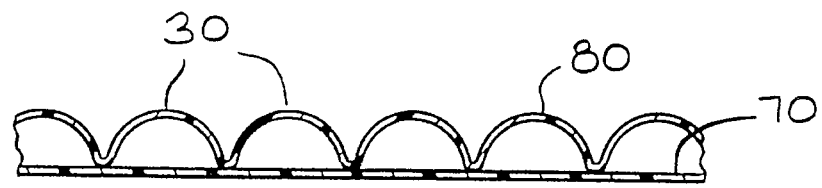
FIG. 11 is a side elevational view showing the second layer joined to the first layer.

As shown in FIG. 11, the joining of the first layer 70 to the second layer 80 forms a plurality of longitudinally extending cylinders 30, as described above. A chamber 30, end walls 22 and 24 and opening 40 can also be formed in the method. The longitudinally extending ends of the joined layers can be brought together and joined by adhesive or otherwise to form the cylindrical tube member 12 shown in FIGS. 1 and 5.

The first layer 70 and second layer 80, as used in the method, can be constructed of a polymer material, as described above for the outer layer 18 and inner layer 20. The second layer 80 is more flexible and is lighter weight than the first layer 70. The cylinders 30 that are formed as a result of the method have the same characteristics as described above concerning the centerline C, radii $R_1$ and $R_2$ and the angle $\beta$ being less than 180°.

The present invention can be modified and changed in a variety of ways with the scope of the invention being defined by the appended claims.

We claim:

1. A method for manufacturing an intraluminal stenting graft comprising a collapsible tube member including an outer layer, an inner layer and a valve positioned in one end of the tube member, said method comprising the steps of:

(a) placing a first layer of material on a substantially flat surface;

(b) placing a second layer of material on a shaped surface;

(c) maintaining said second layer on said shaped surface by use of reverse pressure;

(d) moving said second layer to said first layer;

(e) joining said second layer to said first layer to form a plurality of longitudinally extending cylinders; and (f) shaping said first and second layers to form a tube member.

2. The method of claim 1, wherein said material of said first layer is a polymer material.

3. The method of claim 2, wherein said material of said second layer is a polymer material.

4. The method of claim 3, wherein said material of said second layer is lighter than the material of said first layer.

5. The method of claim 1, wherein said shaped surface is substantially cylindrical.

6. The method of claim 1, wherein each of said cylinders includes a centerline longitudinally extending through said cylinder, said centerline being a point from which two radii extend, said radii defining an angle, said angle being less than 180°.

7. The method of claim 6, wherein said plurality of cylinders are positioned adjacent one another to form said tube member, said radii of one of said cylinders bisecting respective radii of an adjacent cylinder, said cylinders cooperating to prevent said plurality of cylinders from collapsing after said tube member has been expanded.

\* \* \* \* \*